United States Patent [19]

Herpers

[11] 4,401,119
[45] Aug. 30, 1983

[54] PROLONGATION OF TIMING INTERVALS IN RESPONSE TO ECTOPIC HEART BEATS IN ATRIAL AND VENTRICULAR PACEMAKERS

[75] Inventor: Lodewijk-Jozef Herpers, Kerkrade-West, Netherlands

[73] Assignee: Medtronic, Inc., Minneapolis, Minn.

[21] Appl. No.: 235,232

[22] Filed: Feb. 17, 1981

[51] Int. Cl.³ .............................................. A61N 1/36
[52] U.S. Cl. .................................................. 128/419 PG
[58] Field of Search .............................. 128/419 PG

[56] References Cited

U.S. PATENT DOCUMENTS

| | | | |
|---|---|---|---|
| 3,557,796 | 1/1971 | Keller, Jr. et al. | 128/419 PG |
| 3,595,242 | 7/1971 | Berkovits | 128/419 |
| 3,648,707 | 3/1972 | Greatbatch | 128/419 |
| 3,661,158 | 5/1972 | Berkovits | 128/419 |
| 3,669,120 | 6/1972 | Niglsen | 128/419 PG |
| 3,709,229 | 1/1973 | Berkovits | 128/419 |
| 3,759,266 | 9/1973 | Lee | 128/419 |
| 3,768,486 | 10/1973 | Berkovits | 128/419 |
| 3,903,897 | 9/1975 | Woollons | 128/419 |
| 3,985,142 | 10/1976 | Wickham | 128/419 PG |
| 4,108,148 | 8/1978 | Cannon | 128/419 |

FOREIGN PATENT DOCUMENTS 2701104  1/1977  Fed. Rep. of Germany ............ 1/36

OTHER PUBLICATIONS

Irnich, Concept for an Optimum Pacemaker (Translation of Konzept Eines Optimal-Schrittmachers).

Rogel, The Universal Pacer, A Synchronized-Demand Pacemaker, Mar. 1971, pp. 466-471.

Harthorne-Thalen, Boston Colloquim on Cardiac Pacing, 1977, pp. 111-122.

Primary Examiner—William E. Kamm
Attorney, Agent, or Firm—Joseph F. Breimayer; John L. Rooney; Robert C. Beck

[57] ABSTRACT

A programmable pacemaker pulse generator capable of operating in several atrial and ventricular pacing modes, having atrial and ventricular sense amplifiers and output circuits and programmable memory and clock controlled digital timing circuits for selectively delivering stimulating pulses to the heart in an atrial synchronous mode of operation. The ventricular sense amplifier has a blanking and refractory period following the sensing of a ventricular heartbeat or the occurrence of a stimulation pulse. Delay means are operatively connected to the atrial sense amplifier operate to trigger the generation of a ventricular stimulating pulse after an A-V delay interval following a sensed atrial depolarization.

An atrial blanking interval extends for the A-V delay interval and until after the expiration of the ventricular blanking interval. Programmable upper date intervals are also provided.

The ventricular amplifier output is sampled after a test interval shorter than the above mentioned intervals, and if an output signal persists, then all of the aforementioned intervals are prolonged by the interval of the persisting signal.

40 Claims, 4 Drawing Figures

PROLONGATION OF TIMING INTERVALS IN RESPONSE TO ECTOPIC HEART BEATS IN ATRIAL AND VENTRICULAR PACEMAKERS

BACKGROUND OF THE INVENTION

1. Technical Field of the Invention

This invention pertains generally to the field of electrical heart pacemakers, and more specifically to improvements in atrial synchronous pacemakers or other pacemakers capable of operating in an atrial synchronous mode.

2. Description of the Prior Art

Atrial synchronous pacemakers are designed for use on patients whose hearts have normal atrial self pacing, but, due to a defect in the conduction from the atrium to the ventricle, the ventricles fail to beat or keep pace with the atrial rhythm. Atrial synchronous pacemakers are designed to sense the naturally occurring atrial contractions (depolarizations) and, at the end of a short time interval, to provide an electrical stimulation pulse to the ventricles of the heart so as to induce a ventricular contraction. The time delay interval is selected so that the atrial and ventricular contractions are synchronized with an appropriate delay interval for efficient pumping. Atrial synchronous pacing attempts to take the place of missing natural conduction of stimulating pulses from the atrium to the ventricle in the heart, while the heartbeat rate is free to follow, within limits, the natural rhythm established by the atrial self-pacing of the patient. Often other features are combined with atrial synchronous pacing, such as an upper rate limit, or reversion to fixed rate pacing if the spontaneous atrial rate drops below a predetermined rate. Also, provisions may be provided as is known in the art for programming the pacemaker after implantation to adjust the atrial-ventricular delay, upper or lower rates, and other operating parameters. A ventricular inhibit function can also be provided so that if a ventricular depolarization does follow in response to an atrial depolarization, the ventricular depolarization will be sensed and the pacemaker will be inhibited from delivering a competitive ventricular stimulating pulse. In that manner, the stimulating pulses are delivered only if needed.

In addition to atrial synchronous pacemakers, other types of pacemakers capable of operating in a number of modes include atrial synchronous operation as one possible mode of operation. Dual sense-dual pace atrial-ventricular pacemakers, sometimes referred to as fully automatic pacemakers, are capable of selectively delivering stimulating pulses to both the atrium and the ventricle, and are also capable of sensing beats occurring in both chambers and operating as appropriate to maintain A-V synchrony. That type of fully automatic pacemaker will operate in an atrial synchronous mode if the patient's atrium is self pacing above the minimum rate (thus inhibiting delivery of atrial stimulation pulses) and if the ventricles are not contracting on their own at the proper time interval following the atrial contraction, thus resulting in atrial synchronous operation.

Pacemakers operating in an atrial synchronous mode are subject to certain errors which, under certain circumstances, can lead to the delivery of a ventricular stimulating pulse at an inappropriate and possibly dangerous time period of the heartbeat cycle. The problem can occur when a premature ventricular contraction occurs prior to an atrial contraction. Although the atrial sense amplifier is intended to respond only to atrial depolarizations (P-waves) of the electrogram, in fact the R-waves from a ventricular depolarization may be sensed as a P-wave by the atrial sense amplifier. This starts the A-V delay interval, following which the pacemaker delivers a ventricular electrical stimulation pulse. This pulse may fall in time in the vulnerable period of the heart during repolarization from the premature ventricular contraction. Delivery of a stimulation pulse during this vulnerable period is medically unsound, because it could be dangerous to the patient under some circumstances, as it might cause fibrillation of the heart.

It has been recognized in the prior art that the above sequence of events beginning with a premature ventricular contraction and leading to delivery of a ventricular stimulation pulse during the vulnerable period is unacceptable, and various solutions have been proposed. Drug therapy has been used in conjunction with atrial-triggered synchronous ventricular pacemakers in an attempt to suppress premature ventricular contractions so that they would not be detected by the atrial sensing circuit. However, drug therapy has limitations and may be ineffective or inappropriate in certain circumstances and for certain patients. Electronic filtering has also been used in conjunction with the atrial sensing amplifier in order to discriminate the P-wave from the R-wave so as to reject the latter. However, filtration by itself is not workable or reliable in discriminating atrial from ventricular events, because of the inherent variabilities of the shape and frequency composition of R-waves and P-waves in the body. The R-wave in some individuals is more like the P-wave in other individuals, thus greatly complicating any attempt at discrimination by electronic filtering.

In U.S. Pat. No. 4,343,311, there is disclosed an atrial blanking overlap circuit and method for overcoming the above noted problem by sensing both in the atrium and ventricle and by using timing considerations to discriminate between P-waves and R-waves so that a stimulating ventricular pulse is delivered only in response to an actual atrial contraction and not in response to a premature ventricular contraction, when operating in atrial synchronous mode.

The present invention overcomes a further problem arising from strong repolarization voltages present on the ventricular lead arising from a ventricular depolarization or ectopic heart beat ocurring during the preset ventricular blanking period. In certain cases the repolarization voltage may cause the ventricular sense amplifier to register a false sense signal at the end of the ventricular blanking period. In the aforementioned patent application a circuit and method of prolonging the atrial blanking interval was proposed to alleviate false atrial sensing. In the present invention, the appearance of a ventricular sense signal at the end of the ventricular blanking interval further prolongs the ventricular blanking interval, the atrial blanking overlap interval and the ventricular refractory interval by the duration of the false sense signal. In this manner, the circuit advantageously minimizes false ventricular sensing while preserving the atrial blanking overlap.

The invention is useful in both unipolar and bipolar pacemakers, and is particularly useful in unipolar pacemakers, because in the prior art it has been more difficult to discriminate P-waves from R-waves in the case of unipolar pacemakers. The preferred embodiment shown herein is for a unipolar pacemaker.

SUMMARY OF THE INVENTION

According to the present invention there is provided a pacemaker for selectively delivering stimulating pulses to the heart in an atrial synchronous mode of operation, including terminals for connection both to the ventricle and atrium of the patient's heart. Generating means are provided for selectively delivering ventricular electrical stimulation pulses through the ventricular terminal to the ventricle of the heart. A ventricular sense amplifier connects from the ventricular terminal and is operative for sensing ventricular beats of the heart. The ventricular sense amplifier has a blanking and refractory period following the sensing of a ventricular heartbeat or the occurrence of a stimulation pulse. An atrial sense amplifier is connected to the atrial terminal for sensing P-waves indicative of atrial depolarizations, and delay means operatively connected to the atrial sense amplifier operate to trigger the generation of a ventricular electrical stimulating pulse after a predetermined time interval following a sensed atrial depolarization. Control means are operatively associated with the atrial sense amplifier to render it inoperative during the refractory period of the ventricular sense amplifier, so that premature ventricular contractions or other ventricular events will not be erroneously detected by the atrial sense amplifier.

According to the present invention, the atrial sensing amplifier is blanked during the blanking period of the ventricular sense amplifier and also for a predetermined time interval thereafter, so as to avoid detection of ventricular events delayed by the propagation time thereof from a low point in the ventricle to the atrial lead in the heart.

In addition, the atrial blanking period and the ventricular refractory period are prolonged by a ventricular sense signal detected or produced by the ventricular sense amplifier by a time interval and to the actual length of the ventricular sense signal. In this way the time intervals are prolonged to alleviate the possibility of false sensing or that pacing would be triggered into the heart's vulnerable period and to allow the noise sensing circuits to verify the presence (or lack of) noise.

The foregoing and additional advantages and characterizing features of the present invention will become clearly apparent upon reading of the ensuing detailed description of an illustrative embodiment thereof together with the included drawings depicting this theme.

DETAILED DESCRIPTION OF THE PREFERRED EMBODIMENT

Figure 1:
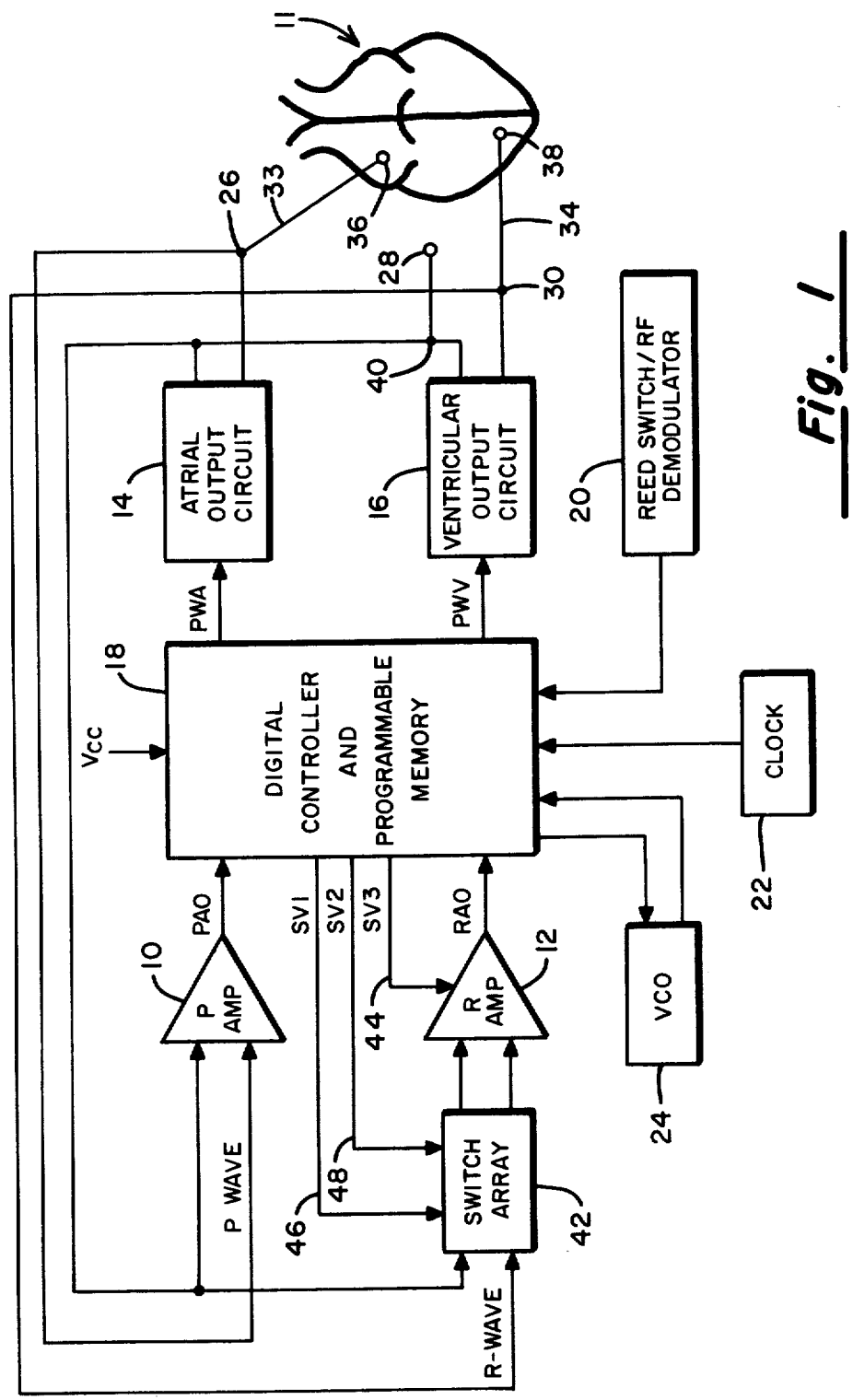
FIG. 1 is a block diagram of a heart pacemaker in which the present invention may be implemented.

In FIG. 1, the major functional elements of a pacemaker in which the present invention can be practised are shown in block diagram form. The pacemaker could either be external or implantable, but in either case it is connected through leads to the patient's heart.

The dual chamber pacemaker of the present invention possesses five basic components in addition to the necessary power supply and leads for conducting electrical signals between the patient's heart and the pacemaker pulse generator. These components are an atrial sense amplifier, a ventricular sense amplifier, an atrial output stage, a ventricular output stage, and a digital controller circuit possessing programmable memory and logic circuits which time the production of atrial and/or ventricular stimulating output pulses as a function of the P-waves sensed by the atrial sense amplifier, R-waves sensed by the ventricular sense amplifier, parameter and mode data stored within the memory, the status of the power source voltage, and the condition of a reed switch which may be effected by an external magnetic field. It is contemplated that in the preferred embodiment of this invention, the pulse generator would be contained within a sealed metallic container electrically connected to the output stages to act as an indifferent electrode and a pair of output connectors or terminals adapted to be coupled by way of leads from the output terminals extending to the atrium and ventricle of the patient's heart.

It is further contemplated that the dual chamber pacemaker of the present invention may automatically operate in several different pacing modes depending on the presence or absence of sensed atrial and/or ventricular depolarizations, that is P-waves and/or R-waves, in a manner described generally, for example, in U.S. Pat. No. 4,312,355. In this context, it is contemplated that several modes of operation may automatically take place depending on the condition of the patient's heart.

Generally, if neither P-waves nor R-waves are present in the atrial and ventricular escape intervals set by the timing circuitry of the pacemaker, it will function in the dual chamber, A-V sequential fixed rate mode (DOO mode as this mode and others referred to herein are designated in the Report of the Inter-Society Commision for Heart Disease Resources in *Circulation*, Vol. L., October, 1974.) If P-waves are not present, but R-waves recur from time to time within the A-V delay interval, the device operates in the A-V sequential demand or DVI mode. If P-waves are present, this device operates in the atrial synchronous or VAT mode in the absence of R-waves sensed within the A-V escape interval or in the atrial synchronous ventricular inhibited (ASVIP) or VDT/I mode when R-waves recur within the A-V interval.

In addition, it is contemplated that the dual chamber pacemaker of the present invention may be externally programmed to operate in a number of different modes including: the fully automatic dual chamber, or DDD mode described above, in which the atrial and ventricular sense amplifiers and the atrial and ventricular output stages are fully operational; in the atrial-ventricular sequential pacing mode, or DVI mode, wherein atrial and ventricular stimulating pulses are provided in timed relationship to one another in the absence of sensed ventricular depolarization; in the atrial synchronous, ventricular inhibited (ASVIP) mode, or the VDT/I mode, wherein the sensed atrial depolarizations cause the pulse generator to deliver a ventricular stimulation pulse unless a spontaneous or conducted ventricular depolarization is detected by the ventricular sense amplifier prior to the timing out of a suitable A-V delay period; or the ventricular demand pacing mode, the VVI mode, wherein the atrial sense amplifier and atrial output stages are not employed.

In addition it is contemplated that the pulse generator can be programmed to operate in the atrial asynchronous mode (AOO), the ventricular asynchronous mode (VOO), or the atrial and ventricular asynchronous modes (DOO), by selectively programming atrial and/or ventricular pulse widths to zero and sensitivity to infinite to arrive at the resulting combination.

Turning now to FIG. 1, there is shown an atrial sense amplifier 10, ventricular sense amplifier 12, atrial output stage 14, ventricular output stage 16, digital control and logic circuit 18, and three further circuits, the RF modulator circuit 20 for receiving remotely applied programming signals and magnetic field test signals, a crystal oscillator 22 for providing the basic clock frequency for the digital control and logic circuit 18, and a voltage controlled oscillator (VCO) circuit 24 for timing certain operations of the digital control and logic circuit 18. The atrial sense amplifier 10 is coupled between the atrial lead terminal 26 and the pulse generator 28 for sensing atrial depolarizations or P-waves. The ventricular sense amplifier 12 is similarly coupled to the case terminal 28 and the ventricular pacing lead terminal 30, for sensing ventricular depolarizations or R-waves. The digital control and logic circuit 18 is coupled to the output terminals of the atrial and ventricular sense amplifiers to receive the atrial amplifier output signal and the ventricular amplifier output signal, to process the signal in accordance with the mode to which the pacemaker is programmed and the parameters of atrial and ventricular timing escape intervals, and to produce, if appropriate, atrial pace initiate signals and ventricular pace initiate signals which are respectively coupled to input terminals of the atrial output stage 14 and the ventricular output stage 16 to initiate respective atrial and ventricular stimulating pulses. The production of the atrial and/or ventricular initiate pulses is dependent upon the presence or absence of sensed atrial and/or ventricular depolarizations of the heart within certain escape intervals established by the parameter data stored in memory within the digital control and logic circuit 18 and dependent upon whether or not the reed switch (circuit 20) is open or closed by the application of an external magnet or on the condition of interference detector (not shown) within the ventricular sense amplifier 12 which responds to noise signals picked up by the ventricular sense amplifier. Ignoring for the moment the possibility of the closure of the reed switch 20 or interference, and turning to the operation of the circuit in the DDD mode, the pulse generator will pace at a programmable lower rate if niether P-waves nor R-waves are sensed within the escape intervals established by lower rate data stored in memory. The A-V interval between the production of atrial and ventricular initiate signals by the digital control and logic circuit 18 is similarly programmable and, under these conditions, the total operation of the pacemaker is characterized as A-V sequential demand pacing.

If a P-wave is sensed by the atrial sense amplifier 10 within the programmed atrial escape interval, (corresponding to a programmable lower rate), the digital control and logic circuit 18 will not produce an atrial pace initiate signal, but instead will commence the timing of the A-V interval. If an R-wave is sensed by the ventricular sense amplifier 12 prior to the expiration of the A-V interval, the ventricular pacing initiate signal is similarly not produced, and all timing intervals will be reset. But if an R-wave is not sensed prior to the completion of the A-V interval, a ventricular pace initiate pulse will be provided by the digital control and logic circuit to initiate the production of a ventricular pacing stimulus at the end of the delay.

If the memory within the digital control and logic circuit 18 is programmed to the VVI mode, the atrial sense amplifier output signal is ignored, and the atrial output initiate signal is not produced. Thus, the digital control and logic circuit 18 responds only to R-waves sensed by the ventricular amplifier 12 and produces only ventricular pace initiate signals in the absence of an R-wave occurring prior to the expiration of the ventricular escape interval.

If the device is programmed in the DVI mode, the atrial output signal of the atrial sense amplifier 10 is similarly ignored. However, the atrial output stage and the ventricular output stage receive atrial and ventricular pace initiate signals at the programmable lower rate and separated by the A-V interval. If an R-wave is sensed during the escape interval and following the refractory period of the ventricular sense amplifier, the lower rate timing is reset. If an R-wave is sensed prior to the completion of the A-V interval and following the delivery of an atrial stimulating pulse to the heart, then the ventricular pace initiate signal is inhibited or not delivered and the lower rate escape interval is again reset.

In the atrial synchronous ventricular inhibited, or VDT/I mode, P-waves recurring at a rate exceeding the programmable lower rate, are sensed by the atrial sense amplifier and processed by the digital control and logic circuit 18 to commence the A-V timing interval. Again, if an R-Wave is sensed prior to the completion of the A-V interval, the ventricular pacing output is inhibited and all timing circuits will be reset. But, if an R-wave is not sensed prior to the completion of the A-V interval, a ventricular pacing stimulus will be provided in response to a ventricular pace initiate signal at the end of the A-V interval. A sensed R-wave occurring within the programmed lower rate escape interval and after the refractory period since the last ventricular depolarization or stimulating pulse, will be processed by the digital control and logic circuit 18 to restart the lower rate timing interval.

The above modes of operation may be selected by the physician to conform the operation of the pacemaker to the patient's condition or the condition of the atrial or ventricular pacing leads. Ordinarily it would be expected that the pacemaker would be left operating in the fully automatic dual chamber or DDD mode, with the lower rate interval, A-V timing interval and other parameters of operation of the device being selected and programmed to conform to the patient's condition.

FIG. 1 also indicates a diagrammatic representation of the patient's heart. A lead 33 extends to the atrium or upper chamber of the heart, and lead 33 has an electrode 36 which contacts the heart at the atrium. Similarly, lead 34 extends to the ventricle or lower chamber of the heart, and it has an electrode 38 at its end which contacts the heart at the ventricle. Although two separate leads 33 and 34 are shown, a single multiple conductor lead having separate electrodes at its tip and at a point along its side may be used for contact with the ventricle and atrium, as is generally known in the art. Leads 33 and 34 connect respectively to terminals 26 and 30 provided on the connector of the pulse generator for connection to the various electrical components and circuits within the pulse generator. An indifferent electrode 28, which may be the pulse generator case, is connected to terminal 40 and the various circuits shown in FIG. 1.

Finally in respect to FIG. 1, the R-wave amplifier 12 is coupled to the switch array 42 into the digital controller and programmable memory 18 through lines 44, 46 and 48 in such a fashion that the ventricular sensing channel of the pulse generator is disconnected from the terminals 28 and 30 for a short interval following the delivery of an atrial stimulating pulse to the terminals 26 and 28. In addition, the signal SV3 is applied to the ventricular amplifier 12 to disable its output for a predetermined time interval following the delivery to the digital controller and programmable memory 18 of the last ventricular sense signal RAO developed by the ventricular amplifier 12. During this interval, the input terminals of the ventricular amplifier 12 are coupled to the terminals 28 and 30, but any signal which is sensed as an R-wave cannot be delivered to the circuit 18. The time duration of the signal SV2 is selected to be somewhat shorter than the ordinary ventricular blanking interval.

Figure 2:
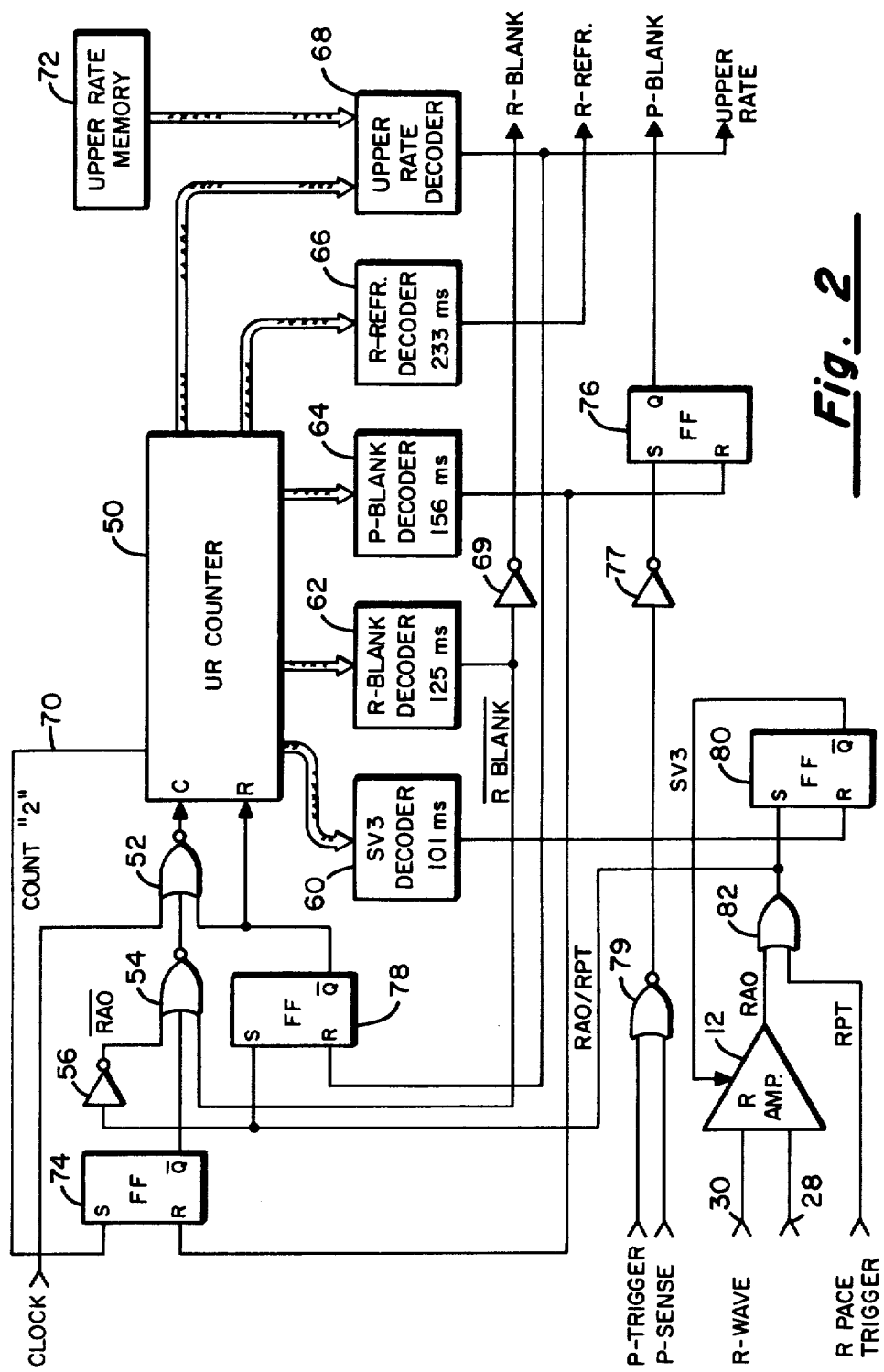
FIG. 2 is a block diagram of the preferred embodiment of the circuit for effecting the blanking interval prolongation of the present invention.

In FIG. 2 the counter 50 is generally referred to as the upper rate counter although it provides the basic timing intervals for the signal SV3, the ventricular or R blank interval, the atrial or P blank interval, the ventricular or R refractory interval and the upper rate interval. The upper rate counter 50 is an up counter which is reset upon reaching the upper rate count and is incremented by clock pulses upon sensing a ventricular depolarization. The low logic level clock pulses are applied to the second input terminal of NOR gate 52, and the output terminal of NOR gate 52 inverts and applies the clock pulses to the clock input of the clock input of the upper rate counter 50 as long as its other two input terminals are low or negative. The first input terminal of NOR gate 52 is coupled to the reset input of counter 50, and the third input terminal of NOR gate 52 is coupled to the output of NOR gate 54. The output of NOR gate 54 is normally low or negative except when all three of its inputs are low or negative, in which case the output goes high and disables the NOR gate 52 from transmitting clock impulses to the counter 50. According to the present invention, the condition in which all three inputs of the NOR gate 54 are low only occurs when the R wave amplifier output signal RAO developed by the ventricular amplifier 12 is present at the end of the ventricular disable interval (SV3). When that occurs, clock impulses are not applied to the counter 50 for the time interval that the signal RAO remains present. Therefore the elapsed time until the expiration of the atrial and ventricular blanking intervals, the ventricular refractory interval and the upper rate interval is extended by the prolonged duration of the signal RAO. This relationship is depicted in FIG. 3b where the prolongation interval is denoted by the letter "X". Clock pulses are also blocked during the interval from the delivery of the upper rate signal (at the end of the upper rate interval) until the next occurrence of the RAO signal.

The upper rate counter 50 consists of a number of flip-flop stages each having a reset input, clock input and bistable outputs all connected in tandem to form a binary counter. In addition, the counter stages are coupled through NAND and NOR gates to form decoding circuits which produce the various signals depicted in FIGS. 3a and 3b. In FIG. 2, the decoding stages are depicted as blocks 60, 62, 64, 66 and 68 and the conductor 70. The ventricular disable interval SV3 is decoded by block 60, the R-blank interval is decoded by block 62, the P-blank interval is decoded by block 64, the R-refractory interval is decoded by block 66, and the upper rate is decoded by block 68. The decoding circuits 60, 62, 64 and 66 and the conductor 70 are preferably implemented in hard wired form; that is, the particular intervals are not programmable or adjustable. In contrast, the upper rate decoding circuit 68 is also coupled to the upper rate memory 72 and is configured in the form of a digital comparator which compares the count in upper rate counter 50 with the upper rate memory count and provides the upper rate signal (and terminates the upper rate interval) when the compared counts are identical. In reference to FIGS. 3a and 3b, the signal in intervals are depicted as positive-going; it will be understood that the signals could and would in fact be employed in their complementary form for purposes of controlling elements of the pulse generator not shown in specific detail in this application.

The interval SV3 provides for testing for a signal at the output of the sense amplifier 12 after 101 ms, for example, and prior to the expiration of the blank interval for the reasons described herein. The R-blank interval of 125 ms is the interval during which the amplifier 12 is normal turned off, except for the test interval when the SV3 signal is developed. The P-blank interval of 156 ms, for example, decoded by 64 is the interval during which the atrial amplifier 10 is disconnected or turned off. The P-blank signal may commence at a P-sense or P-trigger signal preceding an R-sense or R-trigger signal extending through the A-V delay interval and until 31 ms past the expiration of the subsequent R-blank interval. The 31 ms extension (156 ms-125 ms) is call the atrial blank overlap.

The R-refractory interval is the time during which the pulse generator timing (lower rate interval) cannot be reset by ventricular amplifier output (RAO) signals and extends for 233 ms from the preceding sensed or triggered ventricular event. The ventricular refractory interval may also be a longer interval, e.g. 342 ms, upon the detection of an ectopic ventricular depolarization. Ventricular amplifier output (RAO) signals occurring after the R-blank interval and before expiration of the R-refractory interval cause the counter 50 to be reset to reinitiate the timing intervals.

The upper rate count may be selected from a number of programmable upper rate data counts in memory 72, e.g. counts which, when decoded, correspond to upper rates of 100, 125, 150 or 175 bpm.

The conductor 70 represents a hard wired connection to the second stage of the upper rate counter 50 to provide a positive-going signal to the set terminal of flip-flop 74 after two clock impulses are counted by counter 50. When that count occurs, the $\overline{Q}$ output of flip-flop 74 goes low and the low condition is coupled to the first input terminal of NOR gate 54. The reset input terminal of flip-flop 74 is coupled to the P-blank decoding circuit 64 and to the R input of flip-flop 76. Thus the flip-flop 74 is set shortly after the counter 50 begins to count and is reset upon the expiration of the atrial blanking interval whereby a low logic level is maintained on one input terminal of NOR gate 54 for that interval.

The reset inputs of the flip-flop stages of counter 50 are coupled to the $\overline{Q}$ output of reset flip-flop 78. The set and reset inputs of flip-flop 78 are respectively coupled to the outputs of amplifier 12 and the upper rate decoding circuit 68.

The $\overline{Q}$ output of flip-flop 78 is switched high in response to an upper rate signal and resets the counter 50 and also is coupled to the first input terminal of NOR gate 52. NOR gate 52 is therefore incapable of applying the clock input pulses to the counter 50 as long as flip-flop 78 remains reset, and the count remains at zero.

The SV3 decoder 60 provides a signal at the end of the SV3 interval which is applied to the reset terminal of flip-flop 80. The set terminal of flip-flop 80 is connected to the output of OR gate 82 and is normally at a low logic level. The $\overline{Q}$ output provides the normally high SV3 signal to the sense amplifier 12. The SV3 signal is switched low when the R-sense or R-trigger signal is applied to the set terminal and is switched back high after the counter 50 reaches the count decoded by SV3 decoder 60, or 101 ms after the signals RAO or RPT commence the counter's operation.

The output of the P-blank decoder 64 is also applied to the reset termin of flip-flop 76. The set terminal of flip-flop 76 is coupled to the output of inverter 77, which, in turn, is coupled to the output of NOR gate 79. When flip-flop 76 is set, it provides a P-blank interval signal until it is reset by the count, decoded by P-blank decoder 64.

Figure 3A:
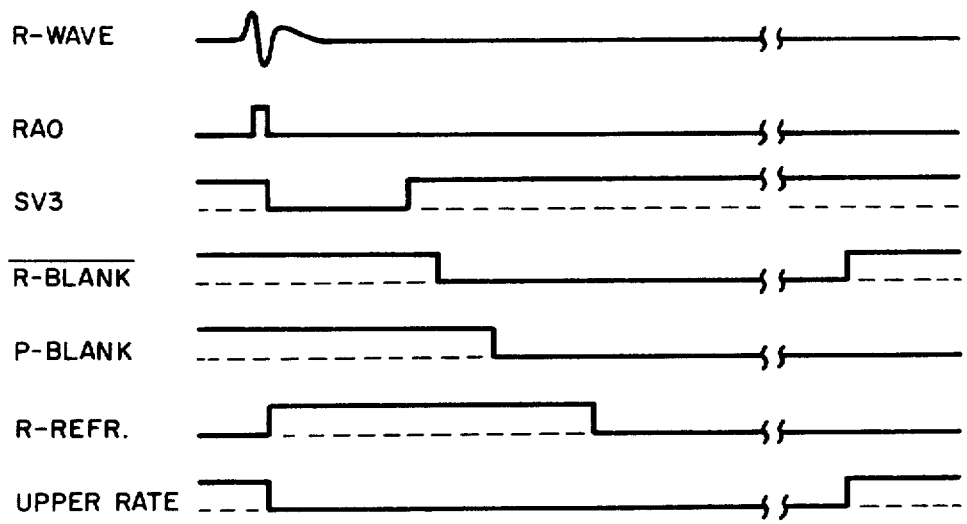
FIGS. 3a and 3b are a graph of pertinent waveforms showing the operation of the circuit of FIG. 2.
Figure 3B:
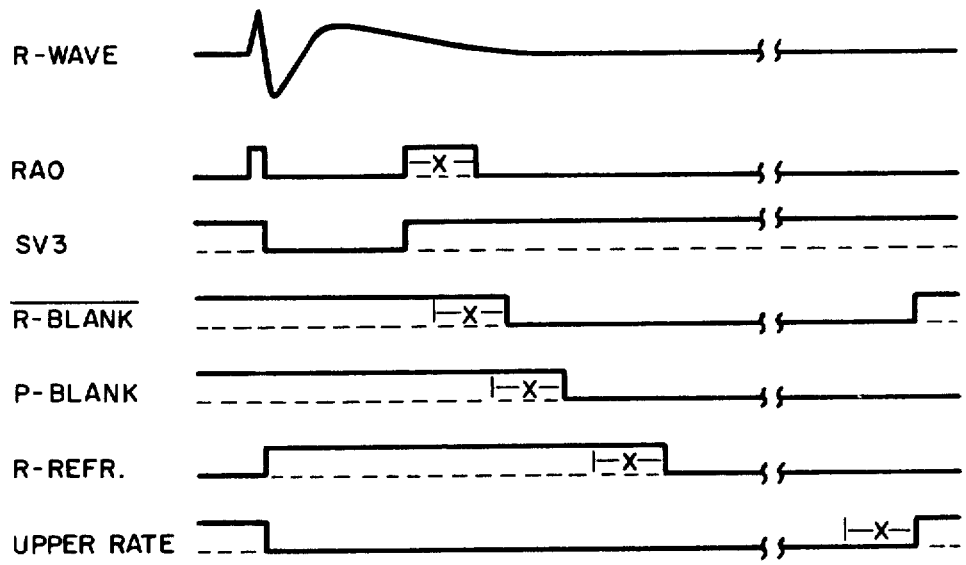

Turning now to the operation of the circuit depicted in FIG. 2, in reference to the timing designs of FIGS. 3a and 3b, it will be assumed that the upper rate counter 50 has in its preceding cycle counted to the upper rate established by the decoding circuit 68 and has been reset to a counter of zero by the reset circuit.

When a ventricular depolarization is sensed by the amplifier 12, the signal RAO is developed and applied through OR gate 82 to the set input of flip-flop 78 which responds by switching to a low logic level at its output $\overline{Q}$. At the same time the inverted signal $\overline{RAO}$ provides a low logic level signal to the first input of NOR gate 54 through inverter 56. The second input of NOR gate 54, coupled to the $\overline{Q}$ terminal of flip-flop 74, is maintained at the high logic level. Therefore the output of NOR gate 54 remains at the low logic level, and clock pulses are in effected conducted through NOR gate 52 to the clock input of counter 50 commencing the counting operation.

Upon the achievement of a count of "two" within the counter 50, the flip-flop 74 is set and switches to low logic level at its $\overline{Q}$ output. However, the $\overline{R\text{-blank}}$ signal remains high, and the output of NOR gate remains low.

The counter 50 continues to count clock pulses, and the SV3 signal decoding circuit 60 and flip-flop 80 produce the signal SV3 when the counter reaches a further count corresponding to the selected time interval such as 101 ms from the detection of the ventricular depolarization. In FIGS. 3a and 3b the time interval SV3 is depicted as a low logic level signal extending from the ventricular event until the expiration of the SV3 time interval, although it will be understood that the decoding circuit 60 does not in fact produce an output signal until it reaches the predetermined count. For purposes of illustration, FIGS. 3a and 3b depict the time interval SV3 during which that signal disables the ventricular amplifier 12 from detecting any further ventricular depolarization. The signal RAO is thus terminated upon generation of the signal SV3.

The counter 50 continues to be incremented by the clock pulses and, shortly after the termination of the SV3 signal, the ventricular blank decoding circuit 62 decodes the count of the ventricular blank interval and terminates the $\overline{R\text{-blank}}$ interval signal. Upon the termination of the $\overline{R\text{-blank}}$ signal, the output of the NOR gate 54 may switch from a low logic level to a high logic level depending on whether or not there exists at that time a signal RAO. If there is no signal RAO at the output of the ventricular amplifier 12, the signal $\overline{RAO}$ is a high logic level signal, and consequently the output of the NOR gate 54 is low regardless of the logic level at its other two inputs. However, as shown in reference to FIG. 3b, an output signal RAO may be present at the output of the ventricular amplifier 12 upon the termination of the signal SV3. In that instance, the high logic level signal RAO is inverted by inverter 56 to provide the low logic level signal $\overline{RAO}$ at the input terminal of NOR gate 54. Since all three input terminals of NOR gate 54 are a low logic level signal, in this instance the output of NOR gate 54 changes to a high logic level. NOR gate 52 is therefore rendered incapable of passing the clock pulses to the input of counter 50, and the counter 50 suspends counting as long as the signal RAO persists at the output of ventricular amplifier 12.

The persistence of the signal RAO would depend, as stated hereinbefore, on the accumulated charge at the electrode surface of the electrode 38 and could occur at high programmed pacing rates and pulse widths in conjunction with particular electrode surface areas or configurations. In this invention, the atrial and ventricular blanking intervals, the ventricular refractory interval and the upper rate limit interval are likewise prolonged to minimize the change that these conditions and the possible condition of extraneous noise could cause the pulse generator to misinterpret the signals and trigger upon a false sensed atrial or ventricular depolarization.

In reference to FIG. 3b, the prolongation of the persisting signal RAO is indicted by the letter "X" which signifies the time interval during which the counter 50 remains at the ventricular blank interval count. Upon the termination of the signal RAO, the signal $\overline{RAO}$ reverts to the high logic level causing the output of NOR gate 54 to revert to the low logic level thus enabling the NOR gate 52.

Consequently, the upper rate counter 50 resumes its count of clock pulses and after achieving a further count, the atrial blank decoding circuit 64 terminates the atrial blank interval signal. The output of the P-blank decoder 64 is applied to the reset terminal of flip-flop 74 and switches the $\overline{Q}$ output to the high logic level. This insures that for the remaining interval through the detection of the next signal RAO and until the counter 50 achieves a count of 2 again, the first input of NOR gate 54 is at a high logic level. The atrial blank or P-blank signal is depicted as a signal applied to the logic circuit within the digital controller and programmable memory 18 which blanks out or ignores any atrial sense signal produced by the sense amplifier 10.

The P-blank interval is provided by the P-blank decoder 64 and the flip-flop 76. The interval extends, when the pulse generator is programmed to operate in the DDD mode, for example, from an atrial event (P-trigger or P-sense) until the ventricular event (R-trigger or R-sense) and from the ventricular event until the P-blank decoder 64 decodes the P-blank count. Thus, the P-blank signal extends from an atrial event through the A-V delay interval and until expiration of the 156 ms plus any prolongation interval "X" from the ventricular event. This interval is provided by flip-flop 76 which is set by the atrial event and reset by the output of decoder 64.

The counter 50 continues to count until it reaches the refractory count and the ventricular refractory decoding circuit 66 terminates the ventricular refractory interval signal. The actual elapsed time of the ventricular refractory signal is extended as shown in FIG. 3b by the prolongation interval X.

Similarly, when the counter 50 reaches the upper rate count, that count is decoded by the upper rate decoding circuit 68 to produce the upper rate signal. That signal is also prolonged by the interval X in the instance when the signal RAO is present at the end of the ventricular blanking interval. The upper rate signal is applied to the reset input terminal of the flip-flop 78 and switches the $\overline{Q}$ output terminal to a high logic level. The high logic level signal is applied to the reset input of the upper rate counter 50 to reset this count to a predetermined start count and is also applied to the first input of the NOR gate 52 to render it incapable of passing clock pulses to the input of counter 50. Thus, counter 50 remains in its initial count condition until the next sensed ventricular depolarization occurs. The then occurring signal RAO is applied to the set input of flip-flop 78 and its $\overline{Q}$ output reverts to the low logic level allowing the output of NOR gate 52 to be switched high each time a clock pulse is applied to its second input. The counter then recommences the counting cycle described hereinbefore.

Thus the circuit depicted in FIG. 2 and described in respect to FIGS. 3a and 3b provides for the prolongation of the atrial blanking interval, the ventricular refractory interval and the adjustment of the upper rate limit under certain conditions wherein the ventricular amplifier output signal RAO persists after the ventricular blanking interval. It will be understood that the invention may be practiced in connection with the fully automatic pacemaker described hereinbefore or in conjunction with a pacemaker designed to perform less than all of the functions of the fully automatic pacemaker such as a simple atrial synchronous ventricular inhibited or VDT/I pulse generator.

The pulse generator as described above conforms to that shown and further described in commonly assigned copending U.S. patent application Ser. No. 235,069, filed Feb. 17, 1981 in my name, which application is hereby incorporated by reference.

The invention may also be implemented in any suitable analog or digital circuitry including software controlled custom or conventional microprocessors. These and other modifications or uses of the invention will be apparent to those skilled in the art.

I claim:

1. A pulse generator for selectively delivering stimulating pulses to the heart in an atrial synchronous mode of operation comprising:
   atrial sensing means for sensing atrial contractions of the heart and providing an atrial sense signal;
   ventricular sense amplifier means for sensing ventricular contractions of the heart and providing a ventricular sense signal;
   ventricular pulse providing means for providing ventricular stimulating pulses in response to an atrial sense signal;
   timing means responsive to a ventricular sense signal for providing a disabling signal for disabling said ventricular sense amplifier means for a first interval following the ventricular sense signal and for providing a further timing signal for controlling the operation of the pulse generator; and
   means responsive to a ventricular sense signal present at the termination of said first interval for suspending operation of said timing means to prolong the time interval of said further timing signal until said ventricular sense signal substantially dissipates.

2. The pulse generator of claim 1 wherein said timing means further comprises:
   means for providing a ventricular sense amplifier blanking signal for a certain interval longer than said first interval, following the ventricular sense signal, whereby said ventricular blanking interval is prolonged by a ventricular sense signal at the end of said first interval.

3. The pulse generator of claim 2 wherein said timing means further comprises:
   means for providing a ventricular refractory signal for a certain interval longer than said first interval following the ventricular sense signal, whereby said ventricular refractory interval is prolonged by a ventricular sense signal at the end of said first interval.

4. The pulse generator of claim 1 wherein said timing means further comprises:
   means for providing a ventricular refractory signal for a certain interval longer than said first interval following the ventricular sense signal, whereby said ventricular refractory interval is prolonged by a ventricular sense signal at the end of said first interval.

5. The pulse generator of claim 1 wherein said suspending means comprises gating means disabled by said ventricular sense signal for operating said timing means for a prolongation interval extending until the ventricular sense signal dissipates.

6. The pulse generator of claim 1 wherein said timing means further comprises:
   clock means for providing clock pulses at a predetermined rate;
   counter means responsive to applied clock signals for changing its count;
   gating means responsive to a ventricular sense signal for applying said clock signals to said counter means; and
   decoding and logic means coupled to said counter means for providing said disabling signal for said first interval following the ventricular sense signal until said counter reaches a first count.

7. The pulse generator of claim 6 wherein said timing means further comprises:
   means for providing a ventricular sense amplifier blanking signal for a certain interval longer than said first interval, following the ventricular sense signal, whereby said ventricular blanking interval is prolonged by a ventricular sense signal at the end of said first interval.

8. The pulse generator of claim 7 wherein said timing means further comprises:
   means for providing a ventricular refractory signal for a certain interval longer than said first interval following the ventricular sense signal, whereby said ventricular refractory interval is prolonged by a ventricular sense signal at the end of said first interval.

9. The pulse generator of claim 6 wherein said timing means further comprises:
   means for providing a ventricular refractory signal for a certain interval longer than said first interval following the ventricular sense signal, whereby said ventricular refractory interval is prolonged by a ventricular sense signal at the end of said first signal.

10. The pulse generator of claim 6 wherein said suspending means comprises gating means disabled by said ventricular sense signal for operating said timing means for a prolongation interval extending until the ventricular sense signal dissipates.

11. The pulse generator of claim 1 wherein said timing means further comprises:
   means for providing ventricular trigger signals at a predetermined lower rate;
   means responsive to a ventricular trigger signal for providing said disabling signal and said further timing signal; and
   wherein said ventricular pulse providing means is also responsive to ventricular trigger signals for providing ventricular stimulating pulses.

12. The pulse generator of claim 11 wherein said timing means further comprises:
   means for providing a ventricular sense amplifier blanking signal for a certain interval longer than said first interval, following the ventricular sense signal, whereby said ventricular blanking interval is prolonged by a ventricular sense signal at the end of said first interval.

13. The pulse generator of claim 12 wherein said timing means further comprises:
   means for providing a ventricular refractory signal for a certain interval longer than said first interval following the ventricular sense signal, whereby said ventricular refractory interval is prolonged by a ventricular sense signal at the end of said first interval.

14. The pulse generator of claim 11 wherein said timing means further comprises:
   means for providing a ventricular refractory signal for a certain interval longer than said first interval following the ventricular sense signal, whereby said ventricular refractory interval is prolonged by a ventricular sense signal at the end of said first interval.

15. The pulse generator of claim 11 wherein said suspending means comprises gating means disabled by said ventricular sense signal for operating said timing means for a prolongation interval extending until the ventricular sense signal dissipates.

16. The pulse generator of claim 11 wherein said timing means further comprises:
   clock means for providing clock pulses at a predetermined rate;
   counter means responsive to applied clock signals for changing its count;
   gating means responsive to a ventricular sense signal for applying said clock signals to said counter means; and
   decoding and logic means coupled to said counter means for providing said disabling signal for said first interval following the ventricular sense signal until said counter reaches a first count.

17. The pulse generator of claim 16 wherein said timing means further comprises:
   means for providing a ventricular sense amplifier blanking signal for a certain interval longer than said first interval, following the ventricular sense signal, whereby said ventricular blanking interval is prolonged by a ventricular sense signal at the end of said first interval.

18. The pulse generator of claim 17 wherein said timing means further comprises:
   means for providing a ventricular refractory signal for a certain interval longer than said first interval following the ventricular sense signal, whereby said ventricular refractory interval is prolonged by a ventricular sense signal at the end of said first interval.

19. The pulse generator of claim 16 wherein said timing means further comprises:
   means for providing a ventricular refractory signal for a certain interval longer than said first interval following the ventricular sense signal, whereby said ventricular refractory interval is prolonged by a ventricular sense signal at the end of said first interval.

20. The pulse generator of claim 16 wherein said suspending means comprises gating means disabled by said ventricular sense signal for operating said timing means for a prolongation interval extending until the ventricular sense signal dissipates.

21. An atrial and ventricular pulse generator comprising:
   atrial sensing means for sensing atrial contractions of the heart and providing an atrial sense signal;
   ventricular sensing means for sensing ventricular contractions of the heart and providing a ventricular sense signal;
   ventricular pulse providing means for providing ventricular stimulating pulses in response to a ventricular trigger signal;
   control means responsive to atrial and ventricular sense signals and selectively providing ventricular trigger signals for triggering said ventricular pulse providing means;
   means for providing a clock signal;
   counting means for counting said clock signals;
   gating means for applying said clock signals to said counting means in response to a ventricular sense signal;
   first decoding means coupled to said counting means for providing a disable interval signal upon a first count of said counting means;
   second decoding means coupled to said counting means for providing a ventricular timing signal upon a further count of said counting means; and
   further gating means responsive to a ventricular sense signal at the termination of the ventricular disable interval signal for suspending the count of said counting means thereby prolonging the interval of the signal provided by said second decoding means until said ventricular sense signal substantially dissipates.

22. The pulse generator of claim 21 wherein said gating means further responsive to a ventricular trigger signal for apply said clock signal to said counting means.

23. The pulse generator of claim 22 wherein said second decoding means further comprises:
   ventricular blank interval decoding means for providing a ventricular blanking signal at a further count of said counting means.

24. The pulse generator of claim 21 wherein said second decoding means further comprising:
   ventricular blank interval decoding means for providing a ventricular blanking signal at a further count of said counting means.

25. The pulse generator of claim 21 wherein said second decoding means further comprises:

ventricular refractory interval decoding means for providing a ventricular refractory signal at a further count of said counting means.

26. The pulse generator of claim 21 wherein said second decoding means further comprises:
atrial blank interval decoding and logic means responsive to an atrial sense signal and a further count of said counter means for commencing and terminating, respectively, an atrial blank interval signal.

27. The pulse generator of claim 26 further comprising:
atrial pulse providing means for providing atrial stimulating pulses in response to atrial trigger signals and wherein:
said control means selectively provides said atrial trigger signals; and
said atrial blank interval decoding and logic means is also responsive to said atrial trigger signals for commencing said atrial blank interval signal.

28. The pulse generator of claim 21 further comprising:
means for providing an upper rate data signal; and wherein said second decoding means further comprises:
upper rate interval decoding means responsive to a further count of said counting means and said upper rate data signal for providing an upper rate signal for controlling the maximum rate of said ventricular pulse providing means.

29. The pulse generator of claim 28 further comprising:
reset means responsive to said upper rate signal for resetting the count of said counter means and disabling said gating means.

30. The pulse generator of claim 29 wherein said second decoding means further comprises:
ventricular refractory interval decoding means for providing a ventricular refractory signal at a further count of said counting means.

31. The pulse generator of claim 30 wherein said second decoding means further comprises:
atrial blank interval decoding and logic means responsive to an atrial sense signal and a further count of said counter means for commencing and terminating, respectively, an atrial blank interval signal.

32. The pulse generator of claim 31 further comprising:
atrial pulse providing means for providing atrial stimulating pulses in response to atrial trigger signals and wherein:
said control means selectively provides said atrial trigger signals; and
said atrial blank interval decoding and logic means is also responsive to said atrial trigger signals for commencing said atrial blank interval signal.

33. The pulse generator of claim 32 further comprising:
means for providing an upper rate data signal; and wherein said second decoding means further comprises:
upper rate interval decoding means responsive to a further count of said counting means and said upper rate data signal for providing an upper rate signal for controlling the maximum rate of said ventricular pulse providing means.

34. The pulse generator of claim 21 wherein said further gating means responds to the count of said counting means as long as the ventricular sense signal persists.

35. An atrial and ventricular pulse generator comprising:
atrial sensing means for sensing atrial contractions of the heart and providing an atrial sense signal;
ventricular sensing means for sensing ventricular contractions of the heart and providing a ventricular sense signal;
atrial pulse providing means for providing atrial stimulating pulses in response to atrial trigger signal;
ventricular pulse providing means for providing ventricular stimulating pulses in response to a ventricular trigger signal; and
digital control and memory means responsive to atrial and ventricular sense signals and selectively providing atrial and ventricular trigger signals for triggering said atrial and ventricular pulse providing means under the control of operating mode and rate control signals further comprising:
first means for commencing a ventricular disable interval signal upon the production of a ventricular sense signal;
second means for providing further signals representing a ventricular blanking interval, an atrial blanking interval and a ventricular refractory interval upon production of a ventricular sense signal; and
third means responsive to a ventricular sense signal at the termination of the ventricular disable interval signal for suspending operation of said second means until dissipation of said ventricular sense signal to thereby prolong the ventricular blanking interval, atrial banking interval and ventricular refractory interval.

36. The pulse generator of claim 35 further comprising:
means for providing a clock signal;
counting means for counting said clock signals;
gating means for applying said clock signals to said counting means in response to a ventricular sense or trigger signal; and wherein:
said first means comprises first decoding means coupled to said counting means for providing a disable interval signal upon a first count of said counting means;
said second means further comprises second decoding means coupled to said counting means for providing a ventricular blanking signal, an atrial blanking signal and a ventricular refractory signal upon further counts of said counting means; and
said third means further comprises gating means responsive to a ventricular sense signal at the termination of the ventricular disable interval signal for suspending the count of said counting means as long as the ventricular sense signal persists thereby prolonging the intervals of the signals provided by said second decoding means.

37. The pulse generator of claim 36 wherein said second decoding means further comprises:
atrial blank interval decoding and logic means responsive to an atrial sense signal and a further count of said counter means for commencing and terminating, respectively, an atrial blank interval signal.

38. The pulse generator of claim 37 further comprising:

said atrial blank interval decoding and logic means is also responsive to said atrial trigger signals for commencing said atrial blank interval signal.

39. The pulse generator of claim 36 further comprising:

means for providing an upper rate data signal; and
wherein said second decoding means further comprises:

upper rate interval decoding means responsive to a further count of said counting means and said upper rate data signal for providing an upper rate signal for controlling the maximum rate of said ventricular pulse providing means.

40. The pulse generator of claim 39 further comprising:

reset means responsive to said upper rate signal for resetting the count of said counter means and disabling said gating means.

* * * * *